(12) United States Patent
Mascal et al.

(10) Patent No.: US 9,868,712 B2
(45) Date of Patent: Jan. 16, 2018

(54) SYNTHESIS OF ALKYLFURANS

(71) Applicant: The Regents of The University of California, Oakland, CA (US)

(72) Inventors: Mark Mascal, Davis, CA (US); Saikat Dutta, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/915,186

(22) PCT Filed: Aug. 29, 2014

(86) PCT No.: PCT/US2014/053402
§ 371 (c)(1),
(2) Date: Feb. 26, 2016

(87) PCT Pub. No.: WO2015/031753
PCT Pub. Date: Mar. 5, 2015

(65) Prior Publication Data
US 2016/0207895 A1 Jul. 21, 2016

Related U.S. Application Data

(60) Provisional application No. 61/872,443, filed on Aug. 30, 2013.

(51) Int. Cl.
*C07D 307/36* (2006.01)

(52) U.S. Cl.
CPC .................. *C07D 307/36* (2013.01)

(58) Field of Classification Search
CPC .................................... C07D 307/36
See application file for complete search history.

(56) References Cited

U.S. PATENT DOCUMENTS

| | | |
|---|---|---|
| 2,297,921 A | 10/1942 | Senkus |
| 2,400,727 A | 5/1946 | Yale |
| 4,335,049 A | 6/1982 | Hamada |
| 8,480,764 B1 | 7/2013 | da Silva Correia |

FOREIGN PATENT DOCUMENTS

| | | |
|---|---|---|
| JP | S5813576 A | 1/1983 |
| TW | 201509925 | 3/2015 |
| WO | 2015031753 A1 | 3/2015 |

OTHER PUBLICATIONS

Brieger & Mestrick, Catalytic Transfer Hydrogenation, 74(5) Chem. Rev. 567-580 (1974).*
International Search Report for International Application No. PCT/US2014/053402 dated Nov. 6, 2014.
Shirini, et al. "Introduction of N-sulfonic acid poly(4-vinylpyridinum) chloride as an efficient and y reusable catalyst for the chemoselective 1, 1-diacetate protection and deprotection of aldehydes", *Journal of Molecular Catalysis A*, vol. 2012 No. 356, pp. 61-69 (2012).
Vincent, et al. "Selective hydrogenolysis of benzyl ethers in the presence of benzylidene acetals with Raney nickel" *Tetrahedron Letters* vol. 47, pp. 4075-4077 (2006).
Mirza-Aghayan, et al. "Palladium chloride-catalyzed reductive cleavage of benzylic acetal, ketal, and ether compounds with triethylsilane" *Iranian Chemical Society* vol. 8, No. 2, pp. 570-573 (2011).
Gong, et al. "Sulfamic acid as a cost-effective and recyclable catalyst for protection of carbonyls to acetals and ketals under mild conditions" *Synthetic Communications* vol. 34, No. 23, pp. 4243-4247 (2004).
Xing, et al. "A solvent-controlled highly efficient Pd-C catalyzed hydrogenolysis of benzaldehydes to methylbenzenes via a novel acetal pathway". *Tetrahedron Letters* vol. 63, pp. 9382-9386 (2007).

* cited by examiner

*Primary Examiner* — Timothy R Rozof
(74) *Attorney, Agent, or Firm* — Mintz, Levin, Cohn, Ferris, Glovsky and Popeo, P.C.

(57) ABSTRACT

The invention provides a method for preparing a 2,5-dialkyl furan. The method includes forming a reaction mixture containing a catalyst, a hydrogen source, and 2-haloalkyl-furan starting material under conditions sufficient to form the 2,5-dialkyl furan. The 2-haloalkylfuran starting material can be derived from biomass, and the 2,5-dialkyl furan product can be used as a biofuel or as a chemical feedstock.

16 Claims, 1 Drawing Sheet

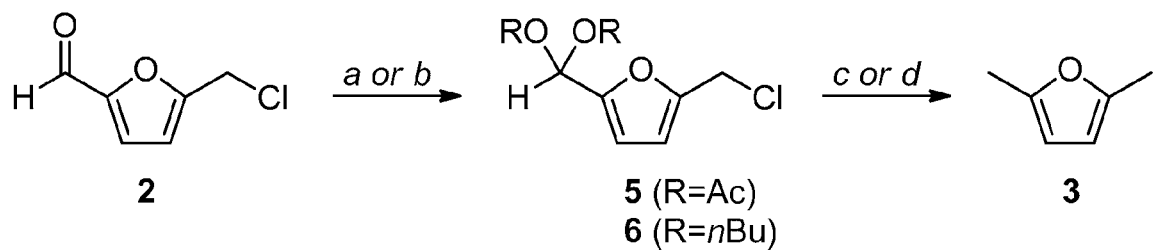
Reagents and conditions: a. Ac$_2$O, Amberlyst-15, 50 °C, 30 min, 92% (of 5); b. BuOH, cat. HCl, 0 °C, 1 h, 98% (of 6); c. H$_2$, Pd/C, HOAc, 30 min, 55% (from 5); d. H$_2$, Pd/C, pentane, 40 min, 82% (from 6).

SYNTHESIS OF ALKYLFURANS

CROSS-REFERENCES TO RELATED APPLICATIONS

The present application is a U.S. national-stage entry of International Patent Application No. PCT/US2014/053402, filed Aug. 29, 2014, and claims priority to U.S. Provisional Patent Application No. 61/872,443 filed Aug. 30, 2013, which applications are incorporated herein by reference in their entirety.

BACKGROUND OF THE INVENTION

The transformation of biomass into fuels and chemicals has received intense global attention in the past decade due to growing concerns over diminishing reserves and volatility in the petroleum market, alongside the environmental impact of releasing vast tonnages of legacy carbon into the atmosphere. The geographic preponderance, renewable nature, and low cost of plant biomass, particularly waste biomass, makes it an ideal resource for sustainable generation of products that would otherwise be derived from petroleum.

Of the approaches to biomass processing that have advanced into commercial practice (microbial, pyrolytic, and chemical-catalytic), a major advantage of the latter is that, in some instances at least, the native structure of the carbohydrate is preserved in the form of the furan ring. Historically, in no case has this been more notable than in the production of 5-(hydroxymethyl)furfural (HMF) 1 from fructose. See, for example, reviews by van Putten and others (e.g., *Chem. Rev.* 2013, 113, 1499). HMF has been cited as a platform molecule of exceptional promise, with multiple applications to polymer, fine chemical, and fuels production. However, the preparation of HMF from sugars other than fructose or from cellulosic sources is complicated by low yields and difficult isolation from aqueous reaction media. As noted in the above-cited review, significant challenges still remain in transitioning HMF production to an industrial scale. No HMF pilot study has successfully employed raw biomass, and although a small number have been operated using sugar feedstocks, this practice is not expected to be economically competitive in the long run.

A solution to the above problem has been proposed in the form of 5-(chloromethyl)furfural (CMF) 2, a stable, hydrophobic analogue of HMF which presents no isolation issues in its production. CMF is prepared under mild conditions and in high yields from sugars, cellulose, or directly from cellulosic biomass by treatment with hydrochloric acid in a biphasic reaction. See, M. Mascal, E. B. Nikitin, *Angew. Chem., Int. Ed.*, 2008, 47, 7924; and M. Mascal, E. B. Nikitin, *ChemSusChem* 2009, 2, 859. While it might be supposed that the requirement for strong acid in this process is disadvantageous, it should be noted that the use of HCl in the chemical industry is long established, and numerous reactor materials have been developed to accommodate it. Multiple technologies for its recovery from solution are also available, including membrane distillation, pervaporation, evaporation, acid base-couple extraction, solvent extraction, diffusion dialysis, and electrodialysis.

The preservation of the furan ring system in 1 and 2 gives access to useful derivative chemistries that other chemical-catalytic routes forfeit, for example those that generate levulinic acid directly from biomass. One of the most sought-after furanics of recent times has been 2,5-dimethylfuran (DMF) 3, and several recent publications have been devoted to its production from HMF 1. In addition to being a high energy density, high octane biofuel, DMF 3 can be converted into p-xylene, a high-volume chemical intermediate used for the production of terephthalate polymers. The potential of 3 to unlock key renewable markets is thus vast.

High yields of DMF 3 from the reduction of HMF 1 have been previously reported. HMF has been hydrogenated using a novel $Ru/Co_3O_4$ catalyst to give DMF in 93% yield, while a bimetallic nickel-tungsten carbide catalyst has been used to provide DMF in 96% yield. PtCo nanoparticles and Ru/C catalysts have afforded DMF in 98% and 95% yields, respectively. However, whether or not these methods are themselves industrially practicable is not so much the point as the fact that they all start from HMF. In effect, no technology is any more scalable than the practical accessibility of its feedstock. Straightforward, industrially viable methods for the production of dialkylfuran products such as DMF are needed. The present invention addresses this and related needs.

BRIEF SUMMARY OF THE INVENTION

In some embodiments, the invention provides a method for preparing a compound of formula I:

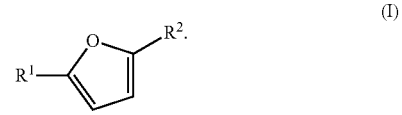

The method includes forming a reaction mixture containing a catalyst, a hydrogen source, and a compound of formula II:

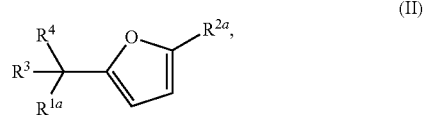

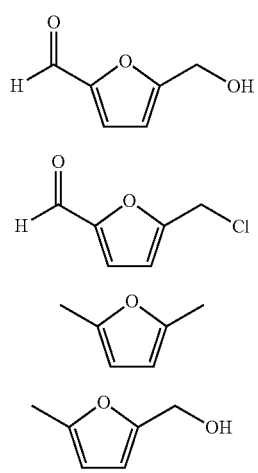

under conditions sufficient to form the compound of formula I;
wherein
$R^1$ and $R^2$ are independently $C_{1-18}$ alkyl;
$R^{1a}$ is selected from H and $C_{1-17}$ alkyl;
$R^{2a}$ is $C_{1-18}$ haloalkyl; and
$R^3$ and $R^4$ are taken together to form oxo (=O); or
$R^3$ is $OR^{3a}$ and $R^4$ is $OR^{4a}$,
wherein $R^{3a}$ is selected from H, $C_{1-6}$ alkyl, and $C_{1-6}$ acyl, and
$R^{4a}$ is selected from $C_{1-6}$ alkyl and $C_{1-6}$ acyl, or
$R^{3a}$ and $R^{4a}$ are taken together to form $C_{2-4}$ alkylene.
In some embodiments, the compound of formula II is a compound of formula IIa:

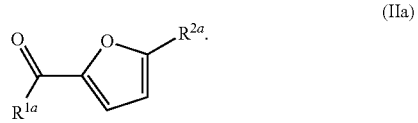

(IIa)

In some embodiments, the compound of formula II is a compound of formula IIb

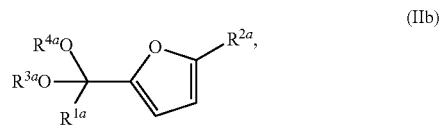

(IIb)

wherein
$R^{1a}$ is selected from the group consisting of H and $C_{1-17}$ alkyl,
$R^{3a}$ is selected from the group consisting of H, $C_{1-6}$ alkyl, and $C_{1-6}$ acyl, and
$R^{4a}$ is selected from the group consisting of $C_{1-6}$ alkyl and $C_{1-6}$ acyl, or
$R^{3a}$ and $R^{4a}$ are taken together to form $C_{2-4}$ alkylene.

In some embodiments, the method further includes forming a first reaction mixture comprising a carbonyl derivatizing agent, an acid, and a compound of formula IIa under conditions sufficient to form the compound of formula IIb. In some embodiments, the compound of formula IIa is 5-(chloromethyl)furfural. In some embodiments, the compound of formula I is 2,5-dimethylfuran.

BRIEF DESCRIPTION OF THE DRAWINGS

FIG. 1 shows a synthetic scheme for preparation of 2,5-dimethylfuran according to methods of the invention.

DETAILED DESCRIPTION OF THE INVENTION

I. General

The present invention allows for the production of dialkylfurans, such as 2,5-dimethyl furfural, that involve the straightforward conversion of biomass-derived starting materials, including 5-(chloromethyl)furfural, into simple derivatives which can be hydrogenated quickly and under very mild conditions, thereby providing renewable routes to valuable dialkylfuran products that avoid the handling of less tractable, commonly-used intermediates such as 5-(hydromethyl)furfural.

II. Definitions

As used herein, the term "alkyl," by itself or as part of another substituent, refers to a straight or branched chain hydrocarbon radical. Alkyl substituents, as well as other hydrocarbon substituents, can contain number designators indicating the number of carbon atoms in the substituent (i.e., $C_1$-$C_8$ designating one to eight carbons), although such designators can be omitted. Unless otherwise specified, the alkyl groups of the present invention contain 1 to 10 carbon atoms. For example, an alkyl group can contain 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 or 5-6 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like. As used herein, the term "alkylene" refers to a divalent alkyl radical. The two points of attachment can be on the same carbon atom in the radical or on different carbon atoms in the radical.

As used herein, the term "haloalkyl" refers to an alkyl group, as described herein, that is substituted with one or more halogen atoms.

As used herein, the terms "halide," "halo," and "halogen," by themselves or as part of another substituent, refer to a fluorine, chlorine, bromine, or iodine atom.

As used herein, the term "acyl," by itself or as part of another substituent, refers to a radical containing an alkyl group, as described herein, bound to the carbon atom of a carbonyl group, the carbonyl carbon atom further being the point of attachment of the radical.

As used herein, the term "aryl" refers to an aromatic ring system having any suitable number of ring atoms and any suitable number of rings. For example, aryl groups can include 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group.

As used herein, the term "oxo" refers to an oxygen atom which is bound to a molecule via a double bond (i.e., a functional group represented by =O).

As used herein, the term "acid" refers to Brønsted acids and Lewis acids. A Brønsted acid is a compound capable of donating a proton (i.e., $H^+$) to a Brønsted base. A Lewis acid is a compound that is capable of accepting electrons from an electron-donating Lewis base and forming a Lewis adduct by sharing the electrons donated by the Lewis base. Examples of acids include, but are not limited to, hydrochloric acid (HCl), acetic acid ($CH_3COOH$), and sulfamic acid ($H_2NSO_3H$).

As used herein, the term "sulfonic acid" refers to an organosulfur compound having the formula $RSO_3H$, wherein R is an alkyl group, a haloalkyl group, or an aryl group as described herein. Examples of sulfonic acids include, but are not limited to, p-toluenesulfonic acid and the like.

As used herein, the term "acidic ion exchange resin" refers to a polymeric resin having a plurality of ionic or ionizable acid functional groups such as sulfonic acid groups.

As used herein, the term "carbonyl derivatizing agent" refers to a chemical reagent that can react with a carbonyl bond (i.e., a carbon-oxygen double bond) to form a dioxy-substituted carbon atom (i.e., a C(OR)(OR') group, wherein R and R' are identical or different carbon-based substituents). Carbonyl derivatizing agents used in the methods of the invention include, but are not limited to, orthoesters, alkanols, and alkanediols.

As used herein, the term "orthoester" refers to a compound having the formula $RC(OR)_3$, wherein each R is an independently-selected alkyl or aryl group as described herein. Examples of orthesters include, but are not limited to, trimethyl orthoformate, triethyl orthoformate, and tripropyl orthoformate.

As used herein, the term "alkanol" refers to an alkyl group, as described herein, having a hydroxy substituent (i.e., an —OH group). Examples of alkanols include, but are not limited to, ethanol, n-butanol, and n-hexanol.

As used herein, the term "alkane-diol" refers to an alkyl group, as described herein, having two hydroxy substituent (i.e., two —OH groups). Examples of alkane-diols include, but are not limited to, ethylene glycol and 1,3-propanediol.

As used herein, the term "acid anhydride" refers to a compound having the formula $RC(O)O(O)CR'$, wherein R and R' are independently-selected alkyl or aryl groups as described herein. Examples of acid anhydrides include, but are not limited to, acetic anhydride and benzoic anhydride.

As used herein, the term "acid chloride" refers to a compound having the formula $RC(O)Cl$, wherein R is an alkyl or aryl group as described herein. Examples of acid chlorides include, but are not limited to, acetyl chloride and trimethylacetyl chloride.

As used herein, the term "forming a reaction mixture" refers to the process of bringing into contact at least two distinct species such that they mix together and can react, either modifying one of the initial reactants or forming a third distinct species, i.e., a product. It should be appreciated, however, that the resulting reaction product can be produced directly from a reaction between the added reagents or from an intermediate from one or more of the added reagents which can be produced in the reaction mixture.

As used herein, the term "catalyst" refers to a substance that participates in a chemical reaction so as to increase the rate of the reaction, but which is itself not consumed in the reaction. Examples of catalysts include, but are not limited to, metals, metal oxides, metal complexes, acids, and bases. The catalysts used in the methods of the invention can be homogenous catalysts, which are present in the same phase as the other reaction components (such as, for example, in solution). The catalysts used in the methods of the invention can also be heterogenous catalysts. Heterogenous catalysts are typically present as solid materials (or immobilized on solid substrates) in reaction mixtures containing solution-phase reactants.

As used herein, the term "hydrogen source" refers to a substance providing hydrogen atoms for transfer to a substrate molecule. Examples of hydrogen sources include, but are not limited to, hydrogen gas, metal hydrides, formic acid, and isopropanol. As used herein, the term "hydrogen gas" refers to molecular hydrogen having the formula $H_2$.

As used herein, the term "transition metal" describes any metal in Groups III through XII of the periodic table. The transition metal can be present in an oxidized state, i.e., having ligands, such as halides or hydroxyl groups, bound to the metal. Alternatively, the transition metal can be present in a reduced state, i.e., in a zero-valent state and which may or may not have ligands bound to the metal.

As used herein, the term "transition metal-based catalyst" refers to a catalyst containing a transition metal. Transition metal catalysts include, but are not limited to, palladium-based catalysts, platinum-based catalysts, rhodium-based catalysts, ruthenium-based catalysts, and nickel-based catalysts. The transition metal in the catalyst can be present in the form of a complex with one or more ligand molecules, or the transition metal can be present in the metallic (i.e., elemental) state in a particulate form, such as a nanoparticulate form. The transition metal can be embedded in, or adsorbed on the surface of, a solid support material such as a polymeric resin, activated charcoal, or an inorganic salt.

As used herein, the term "palladium on carbon" refers to palladium metal that is adsorbed to the surface of a finely divided carbon-based powder such as activated charcoal.

As used herein, the term "5-(chloromethyl)furfural" refers to the compound having the structure:

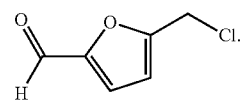

As used herein, the term "2,5-dimethylfuran" refers to the compound having the structure:

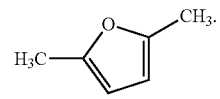

The term "about," as used herein to modify a numerical value, indicates a close range surrounding that explicit value. If "X" were the value, "about X" would indicate a value from 0.9X to 1.1X or a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

III. Methods for Preparing Dialkylfurans

The present invention provides a method for preparing a compound of formula I:

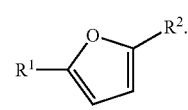

(I)

The method includes:
forming a reaction mixture comprising a catalyst, a hydrogen source, and a compound of formula II:

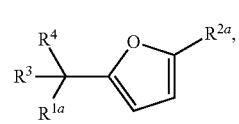

(II)

under conditions sufficient to form the compound of formula I;
wherein
$R^1$ and $R^2$ are independently $C_{1-18}$ alkyl;
$R^{1a}$ is selected from H and $C_{1-17}$ alkyl;

$R^{2a}$ is $C_{1-18}$ haloalkyl; and $R^3$ and $R^4$ are taken together to form oxo (=O); or $R^3$ is $OR^{3a}$ and $R^4$ is $OR^{4a}$, wherein $R^{3a}$ is selected from H, $C_{1-6}$ alkyl, and $C_{1-6}$ acyl, and $R^{4a}$ is selected from $C_{1-6}$ alkyl and $C_{1-6}$ acyl, or $R^{3a}$ and $R^{4a}$ are taken together to form $C_{2-4}$ alkylene.

A. Starting Materials

Furans according to formula II are used as starting materials in the methods of the invention. In some embodiments, the compound of formula II has the formula IIa:

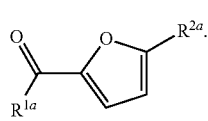

(IIa)

Compounds of formula IIa can be prepared from a number of saccharide materials. Preparation of compounds of formula II from saccharides is described, for example, in U.S. Pat. Nos. 4,154,744; 4,424,390; and 7,829,732; which patents are incorporated herein by reference in their entirety. The saccharide can be a single saccharide or a mixture of saccharides, such as fructose, glucose, mannose, galactose, or sucrose, among others. The saccharide can be a monosaccharide, disaccharide, oligosaccharide, or polysaccharide, or a combination thereof. Monosaccharides include, but are not limited to, glucose, and fructose. Disaccharides include, but are not limited to, sucrose, maltose and lactose. Polysaccharides include, but are not limited to, cellulose, hemicellulose, lignocellulose, and starch. The saccharides can be synthetic or naturally occurring, such as from plant biomass. The saccharides can also be modified, such as by forming esters, or with N-acetyl groups.

Saccharide-containing biomass can include agricultural waste such as corn stover, corn cobs, wheat or oat straw, silage, etc. Useful biomass includes municipal waste, paper products, paper waste, wood residue, agricultural residue (such as plant waste), and energy crops. Forestry waste can include leaves, pine needles, branches, fallen or diseased trees, brush, etc. Domestic waste can include newspaper or other waste paper, waste foodstuffs, vegetation, or processed municipal solid waste from landfills and dump sites. Other saccharides and biomass sources are known to one of skill in the art.

Accordingly, some embodiments of the invention provide methods as described above wherein the compound of formula II is a compound of formula IIa:

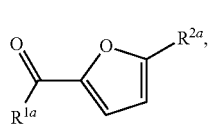

(IIa)

wherein $R^{1a}$ is selected from H and $C_{1-17}$ alkyl; and $R^{2a}$ is $C_{1-18}$ haloalkyl. In some embodiments, $R^{1a}$ is selected from H and $C_{1-17}$ alkyl; and $R^{2a}$ is $C_{1-12}$ haloalkyl. When $R^{1a}$ is H, for example, $R^{2a}$ can be $C_{1-18}$ haloalkyl or $C_{1-12}$ haloalkyl or $C_{1-6}$ haloalkyl or $C_{1-3}$ haloalkyl. When $R^{1a}$ is H, $R^{2a}$ can be $C_1$ haloalkyl (i.e., halomethyl), $C_2$ haloalkyl, $C_3$ haloalkyl, $C_4$ haloalkyl, $C_5$ haloalkyl, $C_6$ haloalkyl, $C_7$ haloalkyl, $C_8$ haloalkyl, $C_9$ haloalkyl, $C_{10}$ haloalkyl, $C_{11}$ haloalkyl, $C_{12}$ haloalkyl, $C_{13}$ haloalkyl, $C_{14}$ haloalkyl, $C_{15}$ haloalkyl, $C_{16}$ haloalkyl, $C_{17}$ haloalkyl, or $C_{18}$ haloalkyl.

In other non-limiting examples of compounds of formula IIa, $R^{1a}$ can be $C_{1-17}$ alkyl; and $R^{2a}$ can be $C_{1-18}$ haloalkyl. In some embodiments, $R^{1a}$ can be $C_{1-17}$ alkyl; and $R^{2a}$ can be $C_{1-12}$ haloalkyl. In some embodiments, $R^{1a}$ can be $C_{1-17}$ alkyl or $C_{1-11}$ alkyl or $C_{1-5}$ alkyl or $C_{1-2}$ alkyl; and $R^{2a}$ can be $C_{1-18}$ haloalkyl or $C_{1-12}$ haloalkyl or $C_{1-6}$ haloalkyl or $C_{1-3}$haloalkyl. When $R^{1a}$ is $C_1$ alkyl, $C_2$ alkyl, $C_3$ alkyl, $C_4$ alkyl, $C_5$ alkyl, $C_6$ alkyl, $C_7$ alkyl, $C_8$ alkyl, $C_9$ alkyl, $C_{10}$ alkyl, $C_{11}$ alkyl, $C_{12}$ alkyl, $C_{13}$ alkyl, $C_{14}$ alkyl, $C_{15}$ alkyl, $C_{16}$ alkyl, or $C_{17}$ alkyl; $R^{2a}$ can be $C_1$ haloalkyl, $C_2$ haloalkyl, $C_3$ haloalkyl, $C_4$ haloalkyl, $C_5$ haloalkyl, $C_6$ haloalkyl, $C_7$ haloalkyl, $C_8$ haloalkyl, $C_9$ haloalkyl, $C_{10}$ haloalkyl, $C_{11}$ haloalkyl, $C_{12}$ haloalkyl, $C_{13}$ haloalkyl, $C_{14}$ haloalkyl, $C_{15}$ haloalkyl, $C_{16}$ haloalkyl, $C_{17}$ haloalkyl, or $C_{18}$ haloalkyl.

Haloalkyl groups in compounds of formula IIa can have one more halogen substituents selected from fluoro, chloro, bromo, and iodo. In some embodiments, the haloalkyl groups have one or more chloro substituents. In some embodiments, the haloalkyl groups have one or more bromo substituents.

One of skill in the art will appreciate that the $R^{1a}$ of formula II, which is H or $C_{1-17}$ alkyl, in combination with the methylene linking $R^{1a}$ to the furan ring, is represented by the $R^1$ of formula I, which can be $C_{1-18}$ alkyl. For example, when $R^{1a}$ of formula II is methyl, $R^1$ of formula I is ethyl. Similarly, one of skill in the art will appreciate that $R^1$ of formula I is methyl when $R^{1a}$ of formula II is H.

In some embodiments, $R^{2a}$ has the formula —(CH)$XR^{2b}$, wherein X is halogen and $R^{2b}$ K is $C_{1-17}$ alkyl. In some embodiments, $R^{2a}$ has the formula —(CH)$XR^{2b}$, wherein X is halogen and $R^{2b}$ is $C_{1-11}$ alkyl. In some embodiments, $R^{2a}$ has the formula —(CH)$XR^{2b}$, wherein X is halogen and $R^{2b}$ is $C_{1-5}$ alkyl. In some embodiments, $R^{2a}$ has the formula —(CH)$XR^{2b}$, wherein X is halogen and $R^{2b}$ is $C_{1-2}$ alkyl. In some embodiments, $R^{1a}$ is H and $R^{2a}$ is selected from chloromethyl, 1-chloroethyl, 1-chloropropyl, and 1-chlorobutyl. In some embodiments, $R^{1a}$ is selected from methyl, ethyl, or butyl; and $R^{2a}$ is selected from chloromethyl, 1-chloroethyl, 1-chloropropyl, and 1-chlorobutyl. In some embodiments, $R^{1a}$ is H and $R^{2a}$ is chloromethyl.

It should be understood that $R^{2a}$ of formula II, which is $C_{1-18}$ haloalkyl, corresponds to $R^2$ of formula I, which is $C_{1-18}$ alkyl. For example, when $R^{2a}$ of formula II is chloromethyl (i.e., —CH$_2$Cl), $R^2$ of formula I is methyl (i.e., —CH$_3$).

In some embodiments, the compound of formula II is a compound of formula IIb

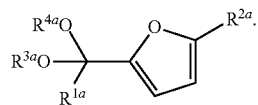

(IIb)

For compounds of formula IIb, $R^{1a}$ is selected from H and $C_{1-17}$ alkyl; $R^{3a}$ is selected from H, $C_{1-6}$ alkyl, and $C_{1-6}$ acyl; and $R^{4a}$ is selected from $C_{1-6}$ alkyl and $C_{1-6}$ acyl. Alternatively, $R^{3a}$ and $R^{4a}$ are taken together to form $C_{2-4}$ alkylene.

In some embodiments, $R^{3a}$ is H and $R^{4a}$ is $C_{1-6}$ alkyl or $C_{1-4}$ alkyl. In some embodiments, $R^{3a}$ is $C_{1-6}$ alkyl or $C_{1-4}$ alkyl and $R^{4a}$ is H. In some embodiments, $R^{3a}$ is $C_{1-6}$ alkyl or $C_{1-4}$ alkyl and $R^{4a}$ is $C_{1-6}$ alkyl or $C_{1-4}$ alkyl. In some embodiments, $R^{3a}$ is $C_{1-6}$ acyl and $R^{4a}$ is $C_{1-6}$ acyl. In some embodiments, $R^{3a}$ is $C_{1-4}$ acyl and $R^{4a}$ is $C_{1-4}$ acyl. In some embodiments, $R^{3a}$ is H and $R^{4a}$ is ethyl or n-butyl. In some embodiments, $R^3$ and $R^{4a}$ are ethyl. In some embodiments, $R^{3a}$ and $R^{4a}$ are n-butyl. In some embodiments, $R^{3a}$ and $R^{4a}$ are acetyl. Compounds of formula IIb can have any combination of $R^{1a}$ and $R^{2a}$ groups, as described above for compounds of formula IIa. Compounds of formula IIb can be prepared from compounds of formula IIa, as described below.

B. Catalysts

Any suitable catalyst can be used for hydrogenation of compounds of formula II. Transition-metal based catalysts—including, but not limited to, palladium-based catalysts, platinum-based catalysts, rhodium-based catalysts, ruthenium-based catalysts, and nickel-based catalysts—are particularly useful in the methods of the invention. The catalyst can be a heterogenous catalyst, which is generally present on a solid support material that does not dissolve in the hydrogenation reaction mixture. Alternatively, the catalyst can be a homogenous catalyst, which is dissolved in the reaction mixture or which is otherwise in the same phase as the compound of formula II.

Examples of homogenous catalysts include, but are not limited to: $RuCl_2(PPh_3)_4$; $RuH_2(PPh_3)_4$; $RuH_2(CO)(PPh_3)_3$; $RuH(CO)Cl(PPh_3)_3$; $RuH(CF_3CO_2)(CO)(PPh_3)_2$; $RuCl_2(PPh_3)_4$; $RuCl_3$; $RhCl(PPh_3)_3$; $RhCl(COHPPh_3)_2$; $RhCl_3 \cdot 3H_2O$; $RhH(PPh_3)_4$; $RhH(CO)(PPh_3)_3$; $IrHCl_2(Me_2SO)_3$; $IrHCl_2(CO)(PPh_3)_2$; $IrH_2Cl(PPh_3)_3$; $IrHCl_2(PPh_3)_3$; $IrH_3(PPh_3)_2$; $IrH_5(PPh_3)_3$; $IrCl(CO)(PPh_3)_2$; $IrBr(CO)(PPh_3)_2$; $IrI(CO)(PPh_3)_2$; $IrH(CO)(PPh_3)_3$; $IrH(COMPPh_3)_2$; $IrCl(C_8H_{12})PPh_3$; $IrH[P(OPh)_3]_4$; $Os(CF_3CO_2)(CO)(PPh_3)_2$; $OsHCl(PPh_3)_3$; $OsH(CO)Cl(PPh_3)_3$; $PtCl_2(PPh_3)_2$; $PtCl_2/SnCl_2$; $K_2PtCl_4$; $PtCl_2(SnCl_2)(PPh_3)_2$; cis-$PtCl_2(PEt_3)_2$; $FeCl_2(PPh_3)_2$; $CoCl_2(PPh_3)_2$; $NiCl_2(Pn-Bu_3)_2$; $ReCl_5$; and $CoH[P(OPh)_3]_3$. The homogenous catalyst can be a palladium catalyst such as a palladium(0) complex [e.g., tetrakis(triphenylphosphine)palladium(0)]; a palladium salt [e.g., palladium(II) acetate, palladium(II) chloride]; or a palladium(II) complex [e.g., allylpalladium(II) chloride dimer, (1,1'-bis(diphenylphosphino)ferrocene)-dichloropalladium(II), bis(acetato)bis(triphenylphosphine)palladium(II), bis(acetonitrile)dichloropalladium(II)].

Examples of heterogenous catalysts include, but are not limited to, pure bulk metals, finely divided metal powders, nanoparticles, porous particulate metals (also known as skeletal or sponge metals), Rieke metals, and metals dispersed on carriers such as carbon (e.g., activated charcoal) or inorganic salts (e.g., calcium carbonate, barium sulfate). Metal alloys containing two or more metals can also be used in bulk form, as powders, nanoparticles, and porous particles, or dispersed on carriers. Heterogenous catalysts include, but are not limited to: Ni (Raney), Pt/C, Pt (black), Rh/C, Rh (black), Ru (black), Ru/C, Ir (black), Pd/Ru, Ni/Cu, Os (black), Co (black), Fe (black), $MgO/SiO_2$, MgO, $Al_2O_3$, In, and $Co/Mo/Al_2O_3$.

Examples of heterogenous palladium catalysts include, but are not limited to, palladium black (elemental palladium), palladium on activated alumina, palladium on carbon, palladium on activated charcoal, palladium on barium sulfate, palladium on calcium carbonate, palladium on strontium carbonate, palladium hydroxide on activated charcoal, palladium hydroxide on carbon, palladium on alumina, palladium on asbestos, and palladium nanoparticles entrapped in aluminum hydroxide matrix. Palladium/lead and palladium/mercury alloys on carbon, calcium carbonate, or barium sulfate carriers can also be used. Heterogenous palladium catalysts typically including from about 0.5% to about 20% palladium by weight. Palladium on carbon, for example, can contain about 5% palladium by weight, or about 10% palladium by weight. Accordingly, some embodiments of the invention provide methods as described above wherein the catalyst is a palladium catalyst. In some embodiments, the catalyst is selected from palladium on carbon, palladium on calcium carbonate, and palladium on barium sulfate. In some embodiments, the catalyst is palladium on carbon.

C. Hydrogen Sources

Any suitable hydrogen source can be used in the methods of the invention. For example, hydrogen gas can be used as the hydrogen source. Hydrogen gas can be used as a pure gas, or as a mixture containing hydrogen gas and an inert gas such as argon or nitrogen. Other examples of hydrogen sources include, but are not limited to: hydrocarbons such as cyclohexene, cyclohexadiene, limonene, indane, and tetralin; alcohols such as ethanol, propan-2-ol, butan-2-ol, pentan-2-ol, benzyl alcohol, phenol, hydroquinone, diphenylmethanol, 1,2-ethanediol, 2,3-butanediol, and 1,2-cyclohexanediol; carboxylic acids such as lactic acid, ascorbic acid, mandelic acid, and formic acid, as well as salts of carboxylic acids such as triethylammonium formate; phosphorus oxoacids such phosphinic acid, and salts of phosphorus oxoacids such as sodium phosphinate; hydride reagents such as sodium borohydride; amines such as isopropylamine and isobutylamine; and other compounds such as hydrazine, hydroxylamine, dioxane, indoline, and N-benzylaniline.

In some embodiments, the hydrogen source is selected from hydrogen gas, a hydrocarbon, an alcohol, a carboxylic acid, a phosphorus oxoacid, and a hydride reagent. In some embodiments, the hydrogen source is selected from hydrogen gas, formic acid, and trimethylammonium formate. In some embodiments, the hydrogen source is hydrogen gas.

D. Hydrogenation Reactions

Dialkylfuran products according to formula I can be prepared by direct hydrogenation of carbonyl-substituted starting materials according to formula IIa. Alternatively, products according to formula I can be prepared via acetal compounds according to formula IIb. In both cases, the hydrogenation conditions are sufficient for reducing the carbonyl or acetal groups and for converting haloalkyl $R^{2a}$ groups to alkyl $R^2$ groups. In certain embodiments, acetal compounds according to formula IIb can be hydrogenated quickly and under very mild conditions.

Accordingly, some embodiments of the invention provide methods wherein the compound of formula II is a compound of formula IIa:

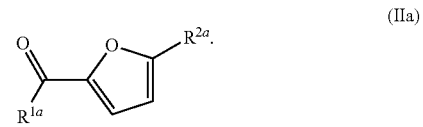

(IIa)

In some embodiments, $R^{2a}$ has the formula —$(CH)XR^{2b}$, wherein X is halogen and $R^{2b}$ is $C_{1-17}$ alkyl. In some embodiments, $R^{2a}$ has the formula —$(CH)XR^{2b}$, wherein X is halogen and $R^{2b}$ is $C_{1-11}$ alkyl. In some embodiments, $R^{2a}$ is chloromethyl. In some embodiments, the compound of formula II is a compound of formula IIa and the hydrogen source is hydrogen gas. In some embodiments, the compound of formula II is a compound of formula IIa and the catalyst is a transition metal-based catalyst. In some embodiments, the compound of formula II is a compound of formula IIa and the catalyst is palladium on carbon.

In some embodiments, the compound of formula IIa is 5-(chloromethyl)furfural. In some embodiments, the compound of formula I is 2,5-dimethylfuran. In some embodiments, the method of the invention includes:

forming a reaction mixture comprising palladium on carbon, hydrogen gas, and a compound of formula IIa having the formula:

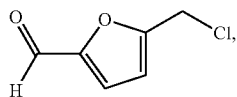

under conditions sufficient to form the compound of formula I having the structure:

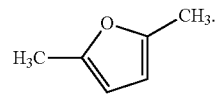

In some embodiments, the compound of formula II is a compound of formula IIb

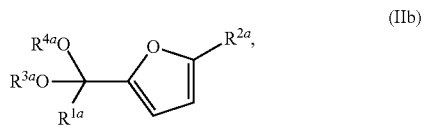

wherein $R^{1a}$ is selected from H and $C_{1-17}$ alkyl; $R^{3a}$ is selected from H, $C_{1-6}$ alkyl, and $C_{1-6}$ acyl; and $R^{4a}$ is selected from $C_{1-6}$ alkyl and $C_{1-6}$ acyl. Alternatively, $R^{3a}$ and $R^{4a}$ are taken together to form $C_{2-4}$ alkylene.

In some embodiments, $R^{2a}$ has the formula $-(CH)XR^{2b}$, wherein X is halogen and $R^{2b}$ is $C_{1-17}$ alkyl. In some embodiments, $R^{2a}$ has the formula $—(CH)XR^{2b}$, wherein X is halogen and $R^{2b}$ is $C_{1-11}$ alkyl. In some embodiments, $R^{2a}$ is chloromethyl.

In some embodiments, the compound of formula II is a compound of formula IIb and the hydrogen source is hydrogen gas. In some embodiments, the compound of formula II is a compound of formula IIb and the catalyst is a transition metal-based catalyst. In some embodiments, the compound of formula II is a compound of formula IIb and the catalyst is palladium on carbon.

Compounds of formula IIb can be prepared from compounds of formula IIa. Accordingly, some embodiments of the invention provide methods further including forming a first reaction mixture comprising a carbonyl derivatizing agent, an acid, and a compound of formula IIa:

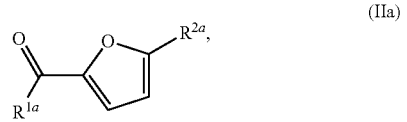

under conditions sufficient to form the compound of formula IIb.

Any suitable acid can be used in the methods of the invention. Examples of useful acids include, but are not limited to, hydrochloric acid, sulfuric acid, nitric acid, acetic acid, trifluoroacetic acid, and sulfamic acid (also referred to as amidosulfonic acid and sulfamidic acid). The acid can also be a sulfonic acid such as methanesulfonic acid, trifluoromethanesulfonic acid, p-toluenesulfonic acid, and the like. The sulfonic acid can be an acidic ion exchange resin such as Dowex-50, Amberlyst-15, or Amberlyst XN-1010.

Any suitable carbonyl derivatizing agent can be used in the methods of the invention. The carbonyl derivatizing agent can be, for example, an orthoester, an alkanol, an alkanediol, an acid chloride, or an acid anhydride. In some embodiments, the carbonyl derivatizing agent can be trimethyl orthoformate, trimethyl orthoacetate, trimethyl orthopropionate, triethyl orthoformate, triethyl orthoacetate, triethyl orthopropionate, trimethyl orthobenzoate, triisopropyl orthoformate, or tripropyl orthoformate. In some embodiments, the carbonyl derivatizing agent can be methanol, ethanol, isopropanol, n-butanol, t-butanol, 3-methyl-2-butanol, 3-pentanol, n-pentanol, 2-methyl-2-pentanol, or n-hexanol. In some embodiments, the carbonyl derivatizing agent can be ethylene glycol, 1,3-propanediol, 1,2-butanediol, or 1,3-butanediol.

In some embodiments, the carbonyl derivatizing agent can be acetic anhydride, benzoic anhydride, succinic anhydride, propionic anhydride, or isobutyric anhydride. In some embodiments, the carbonyl derivatizing agent can be acetyl chloride, benzoyl chloride, propionyl chloride, butyryl chloride, isobutyryl chloride, 2-methylbutyryl chloride, isovaleryl chloride, or trimethylacetyl chloride.

Accordingly, some embodiments of the invention provide methods wherein the first reaction mixture comprises the compound of formula IIa and the carbonyl derivatizing agent is selected from an orthoester, a $C_{1-6}$ alkanol, a $C_{2-4}$ alkane-diol, an acid chloride, and an acid anhydride. In some embodiments, the first reaction mixture comprises the compound of formula IIa and the acid is selected from an acidic ion exchange resin, a sulfonic acid, sulfamic acid, and hydrochloric acid.

In some embodiments, the method of the invention includes:

forming the first reaction mixture comprising acetic anhydride, an acidic ion exchange resin, and the compound of formula IIa having the structure:

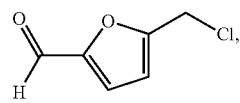

under conditions sufficient to form the compound of formula IIb having the structure:

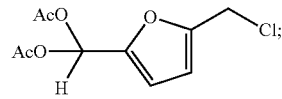

and forming the reaction mixture comprising palladium on carbon, hydrogen gas, and the compound of formula IIb, under conditions sufficient to form the compound of formula I having the structure:

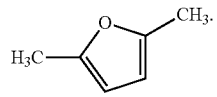

In some embodiments, the method of the invention includes:
forming the first reaction mixture comprising n-butanol, hydrochloric acid, and the compound of formula IIa having the structure:

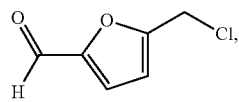

under conditions sufficient to form the compound of formula IIb having the structure:

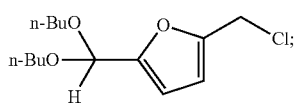

and
forming the reaction mixture comprising palladium on carbon, hydrogen gas, and the compound of formula IIb under conditions sufficient to form the compound of formula I having the structure:

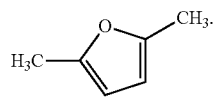

In some embodiments, the method of the invention includes:
forming the first reaction mixture comprising ethanol, hydrochloric acid, and the compound of formula IIa having the structure:

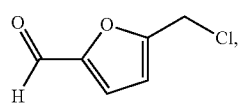

under conditions sufficient to form the compound of formula IIb having the structure:

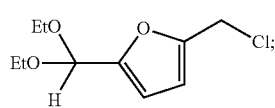

and
forming the reaction mixture comprising palladium on carbon, hydrogen gas, and the compound of formula IIb under conditions sufficient to form the compound of formula I having the structure:

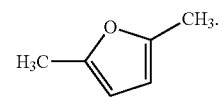

In some embodiments, the reaction mixture comprising the catalyst, the hydrogen source, and the compound of formula II further comprises N,N-dimethylformamide. In some embodiments, the reaction mixture comprising the catalyst, the hydrogen source, the compound of formula II, and N,N-dimethylformamide further comprises acetic acid. In some embodiments, the reaction mixture comprising the catalyst, the hydrogen source, and the compound of formula II further comprises pentane.

In related embodiments, the invention provides a method for preparing a compound of formula XI:

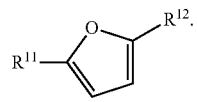

(XI)

The method includes
forming a reaction mixture comprising a catalyst, a hydrogen source, and a compound of formula XII

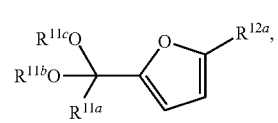

(XII)

under conditions sufficient to form the compound of formula XI,
wherein
$R^{11}$ and $R^{12}$ are independently $C_{1-18}$ alkyl,
$R^{11a}$ is selected from the group consisting of H and $C_{1-17}$ alkyl,
$R^{11b}$ is selected from the group consisting of H and $C_{1-6}$ alkyl,
$R^{11c}$ is $C_{1-6}$ alkyl, or
$R^{11b}$ and $R^{11c}$ are taken together to form $C_{2-4}$ alkylene, and
$R^{12a}$ is $C_{1-12}$ haloalkyl.

Some embodiments of the invention provide a method for preparing a compound of formula XI wherein the hydrogen source is hydrogen gas.

Some embodiments provide a method for preparing a compound of formula XI wherein the catalyst is a transition metal catalyst. Some embodiments provide a method for preparing a compound of formula XI wherein the catalyst is palladium on carbon.

In some embodiments, the invention provides a method for preparing a compound of formula XI further including:
forming a first reaction mixture comprising a carbonyl protecting agent, an acid, and a compound of formula XIII

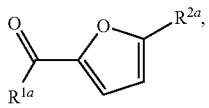 (XIII)

under conditions sufficient to form the compound of formula XII.

Some embodiments provide a method for preparing a compound of formula XI wherein the carbonyl protecting agent is selected from the group consisting of an orthoester, a $C_{1-6}$ alkanol, and a $C_{2-4}$ alkane-diol. Some embodiments provide a method for preparing a compound of formula XI wherein the acid is selected from the group consisting of sulfamic acid and hydrochloric acid.

Some embodiments provide a method for preparing a compound of formula XI wherein the compound of formula XIII is 5-(chloromethyl)furfural. Some embodiments provide a method for preparing a compound of formula XI wherein the compound of formula XI is 2,5-dimethylfuran.

In some embodiments, the invention provides a method for preparing a compound of formula XI including:
  forming the first reaction mixture comprising triethylorthoformate, sulfamic acid, and the compound of formula XIII having the structure:

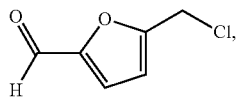

under conditions sufficient to form the compound of formula XII having the structure:

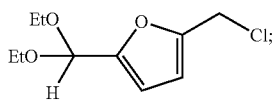

and
  forming the reaction mixture comprising palladium on carbon, hydrogen gas, and the compound of formula XII, under conditions sufficient to form the compound of formula XI having the structure:

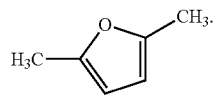

In some embodiments, the invention provides a method for preparing a compound of formula XI including:
  forming the first reaction mixture comprising n-butanol, hydrochloric acid, and the compound of formula XIII having the structure:

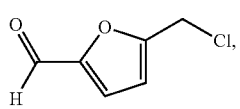

under conditions sufficient to form the compound of formula XII having the structure:

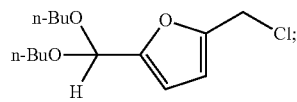

and
  forming the reaction mixture comprising palladium on carbon, hydrogen gas, and the compound of formula XII under conditions sufficient to form the compound of formula XI having the structure:

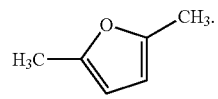

In some embodiments, the reaction mixture comprising the catalyst, the hydrogen source, and the compound of formula XII further comprises N,N-dimethylformamide. In some embodiments, the reaction mixture comprising the catalyst, the hydrogen source, the compound of formula XII, and N,N-dimethylformamide further comprises acetic acid. In some embodiments, the reaction mixture comprising the catalyst, the hydrogen source, and the compound of formula XII further comprises pentane.

E. Compositions

In related embodiments, the invention provides a composition including a catalyst, a hydrogen source, and a compound of formula II:

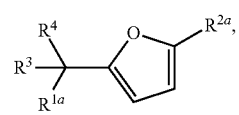 (II)

wherein
  $R^{1a}$ is selected from H and $C_{1-17}$ alkyl;
  $R^{2a}$ is $C_{1-18}$ haloalkyl; and
  $R^3$ and $R^4$ are taken together to form oxo (=O); or
  $R^3$ is $OR^{3a}$ and $R^4$ is $OR^{4a}$,
wherein $R^{3a}$ is selected from H, $C_{1-6}$ alkyl, and $C_{1-6}$ acyl, and $R^{4a}$ is selected from $C_{1-6}$ alkyl and $C_{1-6}$ acyl, or
  $R^{3a}$ and $R^{4a}$ are taken together to form $C_{2-4}$ alkylene.

Some embodiments of the invention provides compositions wherein the compound of formula II is a compound of formula IIa:

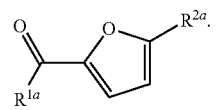 (IIa)

In some embodiments, the invention provides compositions wherein $R^{2a}$ has the formula $-(CH)XR^{2b}$, wherein X is halogen and $R^{2b}$ is $C_{1-11}$ alkyl. In some embodiments, $R^{2a}$ is chloromethyl. In some embodiments, the invention provides compositions wherein the compound of formula II is a compound of formula IIa and the hydrogen source is hydrogen gas. In some embodiments, the invention provides compositions wherein the compound of formula II is a compound of formula IIa and the catalyst is a transition metal-based catalyst. In some embodiments, the invention provides compositions wherein the compound of formula II is a compound of formula IIa and the catalyst is palladium on carbon.

In some embodiments, the invention provides compositions wherein the compound of formula IIa is 5-(chloromethyl)furfural. In some embodiments, the invention provides compositions wherein the compound of formula I is 2,5-dimethylfuran.

In some embodiments, invention provides a composition including palladium on carbon, hydrogen gas, and a compound of formula IIa having the formula:

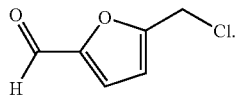

In some embodiments, the invention provides a composition wherein the compound of formula II is a compound of formula IIb

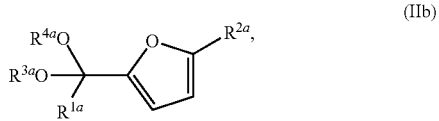

wherein $R^{1a}$ is selected from H and $C_{1-17}$ alkyl; $R^{3a}$ is selected from H, $C_{1-6}$ alkyl, and $C_{1-6}$ acyl; and $R^{4a}$ is selected from $C_{1-6}$ alkyl and $C_{1-6}$ acyl. Alternatively, $R^{3a}$ and $R^{4a}$ are taken together to form $C_{2-4}$ alkylene. In some embodiments, the invention provides a composition wherein $R^{2a}$ has the formula —(CH)$XR^{2b}$, wherein X is halogen and $R^{2b}$ is $C_{1-17}$ alkyl. In some embodiments, the invention provides a composition wherein $R^{2a}$ has the formula —(CH)$XR^{2b}$, wherein X is halogen and $R^{2b}$ is $C_{1-11}$ alkyl. In some embodiments, $R^{2a}$ is chloromethyl.

In some embodiments, the invention provides a composition wherein the compound of formula II is a compound of formula IIb and the hydrogen source is hydrogen gas. In some embodiments, the invention provides a composition wherein the compound of formula II is a compound of formula IIb and the catalyst is a transition metal-based catalyst. In some embodiments, the invention provides a composition wherein the compound of formula II is a compound of formula IIb and the catalyst is palladium on carbon.

In some embodiments, the invention provides a composition containing palladium on carbon, hydrogen gas, and a compound of formula IIb having the structure:

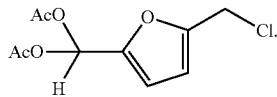 [SMILES: CC(=O)OC(OC(C)=O)c1ccc(CCl)o1]

In some embodiments, the invention provides a composition containing palladium on carbon, hydrogen gas, and a compound of formula IIb having the structure:

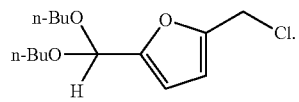

In some embodiments, the invention provides a composition containing palladium on carbon, hydrogen gas, and a compound of formula IIb having the structure:

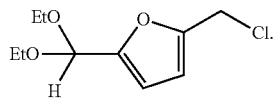 [SMILES: CCOC(OCC)c1ccc(CCl)o1]

In some embodiments, the reaction mixture comprising the palladium on carbon, the hydrogen gas, and the compound of formula II further comprises N,N-dimethylformamide. In some embodiments, the reaction mixture comprising the palladium on carbon, the hydrogen gas, the compound of formula II, and N,N-dimethylformamide further comprises acetic acid. In some embodiments, the reaction mixture comprising the palladium on carbon, the hydrogen gas, and the compound of formula II further comprises pentane.

In related embodiments, the invention provides dialkylfuran compounds according to formula I which are prepared according to the methods described herein. In some embodiments, the invention provides 2,5-dimethylfuran prepared according to the methods described herein.

In some embodiments, the invention provides 2,5-dimethylfuran prepared by a process including forming a reaction mixture comprising 5-(chloromethyl)furfural, palladium on carbon, and hydrogen gas under conditions sufficient to form 2,5-dimethylfuran.

In some embodiments, the invention provides 2,5-dimethylfuran prepared by a process including:
forming a first reaction mixture comprising acetic anhydride, an acidic ion exchange resin, and 5-(chloromethyl)furfural under conditions sufficient to form a compound of formula IIb having the structure:

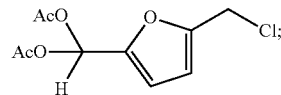

and
forming a second reaction mixture comprising palladium on carbon, hydrogen gas, and the compound of formula IIb under conditions sufficient to form 2,5-dimethylfuran.

In some embodiments, the invention provides 2,5-dimethylfuran prepared by a process including:
forming a first reaction mixture comprising triethylorthoformate, sulfamic acid, and 5-(chloromethyl)furfural under conditions sufficient to form a compound of formula IIb having the structure:

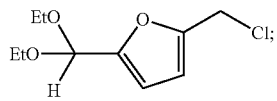 [SMILES: CCOC(OCC)c1ccc(CCl)o1]

and
forming a second reaction mixture comprising palladium on carbon, hydrogen gas, and the compound of formula IIb under conditions sufficient to form 2,5-dimethylfuran.

In some embodiments, the invention provides 2,5-dimethylfuran prepared by a process including:
forming a first reaction mixture comprising n-butanol, hydrochloric acid, and 5-(chloromethyl)furfural under conditions sufficient to form a compound of formula IIb having the structure:

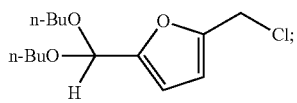

and
forming a second reaction mixture comprising palladium on carbon, hydrogen gas, and the compound of formula IIb under conditions sufficient to form 2,5-dimethylfuran.

F. Reaction Conditions

Any suitable amount of catalyst can be used in the methods of the invention. Typically, a substoichiometric amount of catalyst with respect to the starting materials of formula II is used in the hydrogenation reaction. That is, the number of moles of catalyst in the reaction mixture is less than the number of moles of starting material in the reaction mixture. The molar ratio of catalyst to starting material is generally less than 1:1. In some embodiments, the molar ratio of catalyst to starting material is less than 0.1:1. In some embodiments, the molar ratio of catalyst to starting material is less than 0.01:1. One of skill in the art will appreciate that the molar ratios set forth herein can also be expressed as mole % values and will know how to derive a mole % value from a molar ratio.

The hydrogenation reaction in the methods of the invention can be conducted at any suitable pressure. In general, hydrogenation reactions are conducted at a pressure of at least around atmospheric pressure—i.e., at least around 14.7 pounds per square inch (psi). Hydrogenation reactions can also be conducted at pressures above atmospheric pressure, particularly when hydrogen gas is used as the hydrogen source. For example, hydrogenation reactions can be conducted at about 10 psig, or about 15 psig, or about 45 psig. As used herein, "psig" refers to the pressure relative to atmospheric pressure. Accordingly, "10 psig" indicates an absolute pressure of 10 psi plus 14.7 psi (atmospheric pressure), totaling 24.7 psi. One of skill in the art will appreciate that practical hydrogen pressure levels will depend in part on the particular compound being hydrogenated, as well as on the characteristics or specifications of the reaction vessel and other equipment used for the hydrogenation reaction. Pressures used in a laboratory-scale hydrogenation reaction typically might not exceed around 45 psig, for example, whereas industrial scale reactions can be conducted at pressures around 4000 psig or higher.

The hydrogenation reaction in the methods of the invention can be conducted at any suitable temperature. In general, hydrogenation reactions are conducted at temperatures ranging between about 20° C. and about 200° C. A hydrogenation reaction can be conducted, for example, at from about 20° C. to about 40° C., or from about 20° C. to about 100° C., or from about 40° C. to about 100° C., or from about 20° C. to about 150° C., or from about 100° C. to about 150° C. A hydrogenation reaction can be conducted at about 20, 25, 30, 35, 40, 45, 50, 55, 60, 65, 70, 75, 80, 85, 90, 95, 100, 105, 110, 115, 120, 125, 130, 135, 140, 145, 150, or about 155° C. As for pressure levels used in the methods of the invention, reaction temperatures will depend in part on the particular compound being hydrogenated, as well as on the characteristics and specifications of the equipment used for the hydrogenation reaction.

Any suitable solvent can be used in the methods of the invention. Suitable solvents include, but are not limited to, diethyl ether, diisopropyl ether, ethyl acetate, pentane, hexane, heptane, cyclohexane, benzene, toluene, chloroform, dichloromethane, carbon tetrachloride, 1,2-dichloroethane, 1,1-dichloroethane, N,N-dimethylformamide, N,N-dimethylacetamide, dimethylsulfoxide, N-methyl 2-pyrrolidone, acetic acid, trifluoroacetic acid, trichloroacetic acid, methyl ethyl ketone, methyl isobutylketone, acetonitrile, propionitrile, 1,4-dioxane, sulfolane, 1,2-dimethyoxyethane, and combinations thereof. In some embodiments, the reaction mixture comprises N,N-dimethylformamide. In some embodiments, the reaction mixture comprises N,N-dimethylformamide and acetic acid. In some embodiments, the reaction mixture comprises hexanes or pentane. In some embodiments, the reaction mixture comprises pentane.

Any suitable reaction time can be used in the methods of the invention. In general, reactions are allowed to run for a time sufficient for consumption of the starting material and conversion to the desired product, or until conversion of the starting material comes to a stop. Reactions are typically allowed to run for any amount of time ranging from a few minutes to several hours. Hydrogenation reactions can be run, for example, for anywhere between 5 minutes and 48 hours. Hydrogenation reactions can be run for about 20 minutes, or about 40 minutes, or about 60 minutes. Hydrogenation reactions can be run for about 1.5, 2, 2.5, 3, 3.5, 4, 4.5, 5, 5.5, or 6 hours. In some embodiments, hydrogenation reactions are run for less than 24 hours. In some embodiments, hydrogenation reactions are run for less than 12 hours. In some embodiments, hydrogenation reactions are run for less than 6 hours. Other reaction times can be used in the methods of the invention, depending on the particular hydrogen sources, catalysts, or compounds of formula II that are used.

Products of formula I can be isolated from reaction mixtures via a number of procedures. In some embodiments, the reaction mixture can be cooled to room temperature and the heterogenous catalyst can be removed by filtration. In some embodiments, isolation of the desired product can be achieved via liquid-liquid extraction. For instance, the reaction mixture with can be diluted with water and extracted with a suitable organic solvent, such as diethyl ether. In some embodiments, the extraction process is a continuous extraction process. In some embodiments, products of formula I are isolated by distillation. Combination of isolation methods can also be used in the methods of the invention.

Products of formula I, once prepared according to the methods of the invention, can be utilized for a number of purposes. 2,5-Dimethylfuran (DMF), in particular, can be converted to useful commodity chemicals including paraxylene and terephthalic acid as described, for example, in U.S. Pat. No. 8,314,267 and WO 2013/040514. The chemical and physical properties of DMF, including relatively high energy density and relatively low volatility, also make it an attractive alternative to fossil fuels.

IV. Examples

Materials.

5-Chloromethylfurfural (CMF) was prepared using a published procedure (M. Mascal, E. B. Nikitin, *ChemSusChem*, 2009, 2, 859). 5% Pd/activated carbon, 10% Pd/activated carbon, n-butanol (99%), and 2,5-dimethylfuran (DMF, 99%) were purchased from Sigma-Aldrich and used as received. 5-Methylfurfural (MF, 98%) was purchased from Sigma-Aldrich and freshly distilled prior to use. n-Pentane was purchased from Fisher Scientific and dried over sodium metal before use. N,N-Dimethylformamide (99.8%) was purchased from Acros. Glacial acetic acid and hydrochloric acid (aq., about 37%) were purchased from EMD chemicals and used as received.

Compound Characterization in GCMS.

Mass spectrometry was performed using the EI method starting at 30 m/z. The mass spectra and the retention times matched those of commercially available compounds and literature values from the SDBS database run by the National Metrology Institute of Japan (http://sdbs.riodb.aist-.go.jp/sdbs/cgi-bin/cre_index.cgi).

2,5-Dimethylfuran (CAS#625-86-5) MW 96.13, M.S (EI): m/z (% of max intensity) 50 (22), 51 (27), 53 (85), 67 (13), 81 (40), 88 (6), 95 (76), 96 (100), 97 (7). The observed retention time in the GCMS was 2.47 min.

n-Butanol (CAS#71-36-3) MW 74.12, M.S (EI) m/z (% of max intensity) 53 (2), 55 (19), 56 (100), 57 (8). The observed retention time in the GCMS was 2.12 min.

NMR Data.

$^1$H NMR spectra were recorded using a Varian Merc 300 NMR spectrometer operating at 300 MHz. $^{13}$C NMR spectra were recorded on the same instrument at an operating frequency of 75 MHz. The data were processed using MestReNova (version 6.2.0) desktop NMR data processing software (MestReNova (Mnova), version 6.2.0, Mestrelab Research, SL, Santiago de Compostela, Spain).

Example 1. Hydrogenation of CMF 2 to DMF 3

The direct reduction of CMF to DMF was the starting point for development of the present methods. Initial attempts at the catalytic hydrogenation of CMF led to the formation of DMF in modest yields. CMF 2 (1.00 g) and 10% Pd/C (100 mg) were introduced into 20 mL of cyclohexene and refluxed for 2 h. The $^1$H NMR spectra of the reaction mixture showed only unreacted CMF. The following parameters were changed: (1) loading of catalyst (up to 300 mg), (2) longer time (overnight), (3) solvent (toluene, N,N-dimethylformamide) to dilute cyclohexene. The reaction outcome did not change.

Other transfer hydrogenation reactions were used, including for example, CMF, 10% Pd/C (10 wt % loading) with refluxing isopropanol, and 10% Pd/C with formic acid. However, DMF was not formed as the major product in the above cases and a complex mixture were obtained in each case.

CMF 2 (0.5012 g, 3.467 mmol) was dissolved in N,N-dimethylformamide (5 mL) and 10% Pd/C (50 mg) was added. The reaction flask was purged with hydrogen (×4) and pressurized to 15 psig. The mixture was shaken for 10 min and the pressure was released. The reaction mixture was then diluted with dichloromethane to a volume of 50 mL for analysis by GC-MS (48% yield). The $^1$H NMR spectrum of the reaction mixture also indicated the presence of 5-methylfurfural and 5-methylfurfuryl alcohol alongside a complex mixture of other products.

CMF 2 (0.500 g) and 10% Pd/C (50 mg) were introduced into 10 mL of glacial acetic acid. The mixture was hydrogenated in a Parr hydrogenator at 15 psig hydrogen pressure for 8 min. The $^1$H NMR spectrum showed a mixture of products containing DMF. The selectivity to DMF was 50%.

When neutral solvents like THF, ethyl acetate, alcohols, toluene, and acetonitrile were used for the direct hydrogenation of CMF in the presence of 10% Pd/C catalyst (10 wt % loading) at 15 psig, CMF conversion was complete within 10-12 min. However, decomposition products, colored impurities, and mixtures of products including DMF were observed. Other catalysts (e.g. 5% Pd/C, 5% Pd/BaSO$_4$, 5% Pd/Al$_2$O$_3$, 5% PtO$_2$/C) were used with similar results.

CMF 2 (0.500 g) and 10% Pd/C (50 mg) were introduced into 10 mL of glacial acetic acid and one equivalent of triethylamine (to scavenge HCl). 5-Methylfurfural was formed as the major product (30 min, RT, 15 psig H$_2$). Longer reaction times or higher hydrogen pressures led to 5-methyl-2-furfurylalcohol 4 as the major product.

Example 2. Hydrogenation of CMF 2 to DMF 3

Excellent results were obtained using commercial Pd/C in a 2:1 N,N-dimethylformamide/acetic acid solvent mixture. CMF 2 (2.001 g, 13.84 mmol) was dissolved in a mixture of N,N-dimethylformamide (10 mL) and glacial acetic acid (5 mL) in a 250 ml, glass vessel. Pd/C (5 wt %, 200 mg, 0.68 mol % loading of Pd) was added and the vessel was purged with hydrogen (×4) and pressurized to 43 psig. The mixture was shaken in a Parr hydrogenator for 1 h 15 min at RT while maintaining the initial pressure. The hydrogen gas was released and the reaction mixture was diluted with dichloromethane and transferred into a 1 L volumetric flask for analysis by GCMS using dodecane as the internal standard. Alternatively, the yield of DMF was determined by quantitative $^1$H NMR spectroscopy using methyl benzoate as the internal standard. The details of yield determination by GCMS and quantitative $^1$H NMR spectroscopy are given below. The conditions were remarkably mild (room temperature, 3 atm H$_2$, 1.25 h), particularly compared to those typically used for the hydrogenation of HMF (130-200° C., 7-40 atm H$_2$, 2-24 h), and provided DMF 3 in 76% yield.

Example 3. Hydrogenation of CMFDA 5 to DMF 3

The direct hydrogenation of CMF proceeds via 5-methylfurfuryl alcohol 4, which is unstable under the reaction conditions and appears to be responsible for the formation of side products which limit the selectivity to 3. In an effort to bypass the formation of 4 and hence the issues associated with its intermediacy during the reduction of CMF, indirect approaches to the reduction of aromatic aldehydes were developed.

The diacetoxy acetal of CMF, namely 2-(chloromethyl)-5-(diacetoxymethyl) furan 5, was prepared in high yield by the solvent-free reaction of 2 with acetic anhydride in presence of an acidic Amberlyst resin catalyst. See, FIG. 1.

(5-(Chloromethyl)furan-2-yl)methylene diacetate (CMFDA) 5

To a solution of CMF 2 (0.500 g, 3.46 mmol) in acetic anhydride (1.412 g) was added Amberlyst-15 (100 mg) and the mixture was heated at 50° C. for 30 min. The excess acetic anhydride was evaporated under reduced pressure and the residue was dissolved in dichloromethane (10 mL), filtered, and passed through a plug of silica (dichloromethane). Evaporation of the solvent gave 5 (0.785 g, 92%) as a yellow, crystalline solid. $^1$H NMR (CDCL$_3$, 300 MHz) 7.65 (1H, s), 6.45 (1H, d, 3.0 Hz), 6.34 (1H, d, 3.0 Hz), 4.54 (2H, s), 2.10 (6H, s). $^{13}$C NMR (CDCL$_3$, 75 MHz) 168.3, 151.4, 148.5, 110.8, 110.3, 83.2, 37.0, 20.7.

Compound 5 (1.001 g, 4.059 mmol) was dissolved in glacial acetic acid (10 mL) and 10% Pd/C (200 mg) was added. The suspension was purged with hydrogen (×4) before pressurizing to 30 psig. The mixture was hydrogenated in a Parr shaker for 30 min at RT while maintaining the initial pressure. A measured volume (1.00 mL) of the reaction mixture was taken in a syringe and transferred into a 5 mL volumetric flask. Methyl benzoate was added as the internal standard and the flask was filled to the mark with CDCl$_3$ for $^1$H NMR quantification. The yield of DMF 3 was calculated to be 55%, with evidence of ring reduction and other by-products being formed.

Example 4. Preparation of DMF via 2-(chloromethyl)-5-(diethoxymethyl)furan (CMFDEA)

To a solution of CMF 2 (0.500 g, 3.46 mmol) in triethylorthoformate (0.75 mL, 0.67 g, 4.5 mmol) was added sulfamic acid (0.050 g, 0.52 mmol). The flask was purged with argon and the mixture was stirred at room temperature for 5 h. Pentane (10 mL) was added and the mixture was stirred an additional 5 min, during which the sulfamic acid precipitated out as a white solid. The solution was filtered through Celite, the solids were washed with pentane (10 mL), and the combined organic layers were evaporated to yield CMFDEA as a light yellow liquid (0.7103 g, 94%). $^1$H NMR (CDCl$_3$, 300 MHz) 6.33 (1H, d, J=3.0 Hz), 6.29 (1H, d, J=3.0 Hz), 5.48 (1H, s), 4.54 (2H, s), 3.58 (4H, m), 1.19 (6H, t, J=7.2 Hz). $^{13}$C NMR (CDCl$_3$, 75 MHz) 153.03, 150.15, 110.43, 109.29, 96.28, 61.54, 37.66, 15.30. HRMS: (M-OEt)$^+$ C$_8$H$_{10}$O$_2$Cl$_1$, calculated 173.0369, found 173.0361.

To a solution of CMFDEA (1.00 g, 4.60 mmol) in p-xylene (10 mL) was added 5% Pd/C (0.10 g). The mixture was purged with hydrogen (×4) and the reaction flask was pressurized to 15 psig, which was maintained during the reaction. The mixture was shaken for 40 min, after which the flask was cooled in an ice bath and the hydrogen pressure released. The resulting colorless solution was diluted with dichloromethane to a volume of 100 mL for analysis by GC-MS (88% yield).

Example 5. Hydrogenation of CMFDBA 6 to DMF 3

Although dialkyl acetals can be prepared from aldehydes by the use of orthoformate reagents, and the diethyl acetal of CMF can be made by this method, avoiding the generation of a formate ester by-product can be advantageous. The question was whether CMF would withstand standard acetalization conditions (i.e., alcohol plus strong acid catalyst). n-Butanol was selected as the alcohol of choice due to its renewable production from biomass, low cost, low volatility, low toxicity, and the favorable formation of a low-boiling azeotrope with water. When CMF was treated with n-butanol in presence of a catalytic amount of acid (HCl), 2-(chloromethyl)-5-(dibutoxymethyl)furan 6 was obtained in 98% isolated yield.

The hydrogenation of 6 using a Pd/C catalyst attempted in the absence of solvent gave DMF 3 as the major product, but a colored impurity and some side products were also observed. Careful analysis showed that the acetal functionality in 6 was being compromised to some extent due to the liberation of HCl during reduction of the chloromethyl group, leading to alternative reaction pathways. However, when the reaction was conducted in the presence of an inert solvent (pentane), an 82% yield of DMF was obtained. Operationally, CMF is dissolved in butanol, a couple drops of concentrated aqueous HCl are added and the butanol is then removed under reduced pressure. The residue (6) is dissolved in pentane and subjected to a slight overpressure (10 psig) of hydrogen in the presence of 5% Pd/C at room temperature for 40 minutes, after which the catalyst is filtered off. The wide gap in boiling points (pentane 36° C., DMF 3 93° C., butanol 118° C.) ensures the facile separation of the components by fractional distillation. The atom-economy of the process is excellent since water is the only by-product, with everything else being used in a cycle (hydrogen chloride can be recovered and reapplied to the synthesis of CMF).

2-(Chloromethyl)-5-(dibutoxymethyl)furan (CMFDBA) 6

To a solution of CMF 2 (2.000 g, 13.84 mmol) in n-butanol (40 mL) was added 37% aq. HCl (0.10 mL). The solvent was evaporated at RT using a rotary evaporator at a bath temperature <10° C. under vacuum (10 mm Hg). The product 6 was obtained as a light yellow liquid (3.721 g, 98%) which could be used in the next step without further purification. $^1$H NMR (CDCl$_3$, 300 MHz) 6.32 (1H, s), 6.29 (1H, s), 5.47 (1H, s), 4.53 (2H, s), 3.51 (4H, m), 1.52 (4H, m), 1.35 (4H, m), 0.88 (6H, t, J=7.3 Hz). $^{13}$C NMR (CDCl$_3$, 75 MHz) 153.09, 150.11, 110.39, 109.35, 96.48, 65.69, 37.67, 31.90, 19.54, 14.04. HRMS: (M-OBu)$^+$ C$_{10}$H$_{14}$O$_2$Cl$_1$, calculated 201.0682, found 201.0678.

To a solution of 6 (10.00 g, 36.40 mmol) in pentane (100 mL) was added 5% Pd/C (0.50 g). The mixture was purged with hydrogen (×4) and the reaction flask was pressurized to 10 psig, which was maintained during the reaction. The mixture was shaken for 40 min, after which the flask was cooled in an ice bath and the hydrogen pressure released. The resulting colorless solution was diluted with dichloromethane to a volume of 250 mL for analysis by GC-MS (93% yield).

In another reaction, compound 6 (2.002 g, 7.286 mmol) was dissolved in n-pentane (10 mL) and 5% Pd/C (0.100 g, 0.64 mol % loading of Pd) was added. The suspension was purged with hydrogen (×4) before pressurizing to 10 psig. The mixture was hydrogenated in a Parr shaker for 40 min at RT while maintaining the initial pressure. The vessel was cooled in an ice water bath before releasing the hydrogen pressure. The light yellow reaction mixture was transferred into a 500 mL volumetric flask and filled to the mark with dichloromethane for GCMS quantification with dodecane as the internal standard. Alternatively, the yield of DMF 3 was measured by quantitative $^1$H NMR spectroscopy using methyl benzoate as an internal standard, as described in the following sections.

Example 6. Preparation of DMF 3 Via CMF Derivatives

CMFDBA (2.00 g) and 100 mg 5% Pd/C were introduced into Na-dried THF (10 mL). The mixture was hydrogenated in a Parr shaker hydrogenator at 10 psig hydrogen pressure for 30 min at RT. DMF 3 was found to be the major product along with minor ring saturation products. The yield determination by quantitative ¹H NMR gave 65% yield of DMF 3. Reaction time, catalyst loading, and amount of solvent were varied but formation of ring saturation product could not be avoided.

Use of dry toluene or dry p-xylene (10 mL) as solvent for the hydrogenation of CMFDBA (2.00 g) in presence of 5% Pd/C (100 mg) for 40 min at 10 psig hydrogen pressure gave 70% DMF yield (¹H NMR spectroscopy). Use of other common hydrogenation solvents like ethyl acetate or 1-butanol gave a mixture of products along with colored impurities, and the selectivity to DMF was low (>30%).

Pure CMFDEA or pure CMFDMA were prepared by the reaction of CMF 2 with triethylorthoformate and trimethylorthoformate, respectively, using sulfamic acid as catalyst. Catalytic hydrogenation of CMFDEA or CMFDMA in presence of 5% Pd/C also led to DMF formation. However, the yield of DMF was 10% lower than CMFDBA. Pentane was found to be a particularly useful solvent.

CMFEGA (ethylene glycol) and CMFPGA (propylene glycol) were synthesized by the reaction of CMF 2 with excess ethylene glycol and propylene glycol respectively with a catalytic amount of concentrated aqueous HCl as the catalyst. The CMFEGA or CMFPGA thus produced contained around 3-5% CMF. Forcing the reaction with longer time, or higher temperature led to substitution of the chloromethyl group. Even when pure CMFEGA or CMFPGA (1.00 g) were used for the hydrogenation using 5% Pd/C (50 mg) in dry THF (10 mL), DMF was formed as the major product along with ring saturation product. The ¹H NMR integration showed DMF in 70% yield. The reaction was fast (25 min at 10 psig $H_2$ pressure) but ring saturation was typically observed for various reaction conditions.

When CMFDBA (2.00 g), 5% Pd/C (50 mg), and 10 mL Na-dried pentane was hydrogenated at 10 psig $H_2$ pressure at RT for 40 min in presence of organic bases like triethylamine (1 eq.), the reaction did not form DMF. The reaction formed colored impurities, some deprotected product (CMF), 5-methylfurfural, and starting material. When less than 1 eq. triethylamine was used, DMF formed as a minor but colored impurities still formed.

When CMFDBA (2.00 g), 5% Pd/C (50 mg), and 10 mL Na-dried pentane was hydrogenated at 10 psig $H_2$ pressure at RT for 40 min in presence of proton sponges like triphenylphosphine or $[Cu(3-Cl-pyridine)_2Cl_2]$, the reaction stopped completely and only CMFDBA was recovered after reaction.

Example 7. Yield Determination by Quantitative ¹H NMR

After each hydrogenation reaction, the total volume of the reaction mixture was accurately measured. 1.00 mL of this mixture was taken via microliter syringe and transferred into a 5 ml volumetric flask. A measured mass of methyl benzoate was added as an internal standard and the flask was filled to the mark with $CDCl_3$. An ¹H NMR spectrum of the solution was recorded and the peaks were integrated. The peak for the methyl group (three protons) in methyl benzoate and methyl groups in DMF 3 (six protons) were used to quantify the yield.

Yield of the Hydrogenation of CMF 2 to DMF 3.

The reaction was carried out using the procedure described above. The measured volume of the solution after hydrogenation reaction was 16.0 mL.

The theoretical yield of DMF (MW=96.13) from 2.001 g of CMF (MW=144.55) is 1.331 g. The amount of methyl benzoate (MW=136.15) added into the 5 mL volumetric flask as an internal standard was 0.125 g. The methyl group of methyl benzoate was integrated to 3.00 and the integration of the methyl groups (six protons) in DMF was 4.28. Thus, the amount of DMF in the 5 mL volumetric flask was 0.063 g DMF. Since only 1.00 mL of the total 16.0 ml, reaction mixture was taken in the volumetric flask, the total amount of DMF generated was (0.063×16)=1.008 g. Thus, the percent yield of DMF was (1.008 g/1.331 g)×100%=76%.

Example 8. Yield Determination by GCMS

General Procedure.

GCMS was performed using a Shimadzu GCMS-QP2010S instrument with SHR5XLB column (length 30 m, diameter 0.25 mm, thickness 0.25 μm) employing hydrogen gas as the mobile phase. The initial oven temperature and injection temperature were set to 40° C. and 250° C., respectively. The temperature was increased by 2° C./min until the oven temperature reached 44° C. After reaching 44° C., the temperature was ramped up 20° C./min until 126° C., and then increased to 130° C. by 2° C./min. The solvent cutoff was set to 1.5 min. The column pressure started at 46 kPa and reached 74 kPa at 130° C. The column flow was 2.14 mL/min whereas total flow was 6.9 mL/min. The response factor for DMF was calculated from five standard solutions of known concentration using commercial DMF (Sigma Aldrich, 99%) with dodecane as the internal standard.

| | Mass of DMF (mg) | Concentration of DMF (mM) | Area of DMF | Mass of dodecane (mg) | Concentration of dodecane (mM) | Area of dodecane | Response factor |
|---|---|---|---|---|---|---|---|
| 1 | 29.6 | 6.16 | 117623 | 61.6 | 7.23 | 463240 | 0.30 |
| 2 | 45.4 | 9.45 | 168068 | 56.5 | 6.63 | 168068 | 0.26 |
| 3 | 62.7 | 13.0 | 243046 | 58.1 | 6.82 | 243046 | 0.32 |
| 4 | 81.2 | 16.9 | 356312 | 59.6 | 7.00 | 482468 | 0.30 |
| | | | | Average response factor | | | 0.29 |

Four standard solutions of DMF of known concentration were prepared with a measured amount of dodecane added as an internal standard. In a 50 mL volumetric flask, measured masses of DMF and dodecane were added, followed by AcOH (0.25 mL) and N,N-dimethylformamide (1.0 mL). The flask was then filled up to the mark using dichloromethane. Since the reaction mixture also contained AcOH and N,N-dimethylformamide, they were also included as standards to minimize any matrix effect.

Yield of the Hydrogenation of CMF 2 to DMF (3).

The reaction details are reported above. CMF used=2.001 g. Total volume after reaction was 16.0 mL. The reaction mixture was transferred into a 1 L volumetric flask. Dodecane (1.216 g, 0.00714 M) was added as an internal standard and the flask was filled up to the mark with dichloromethane. The area observed for DMF was 195672, and the area observed for dodecane was 436471. The amount of DMF in the volumetric flask was determined using the following calculation:

$$\frac{Area\ of\ DMF}{R} \times \frac{Conc.\ of\ dodecane}{Area\ of\ dodecane} =$$

-continued $$\frac{195672}{0.29} \times \frac{0.00714 \,\text{M}}{436471} = 0.0110 \,\text{M} = 1.061 \,\text{g}$$

The theoretical yield of DMF from 2.001 g of CMF was 1.331 g, and the percent yield calculated by GCMS was 80%.

Four standard solutions of DMF of known concentration were prepared with a measured amount of dodecane added as an internal standard. In a 50 mL volumetric flask, measured masses of DMF and dodecane were added, followed 1 mL of pentane. The flask was filled up to the mark using dichloromethane. Since the reaction mixture uses pentane as solvent, it was included as a standard to minimize any matrix effect.

| | Mass of DMF (mg) | Concentration of DMF (mM) | Area of DMF | Mass of dodecane (mg) | Concentration of dodecane (mM) | Area of dodecane | Response factor |
|---|---|---|---|---|---|---|---|
| 1 | 31.4 | 6.53 | 60771 | 66.0 | 7.75 | 398589 | 0.18 |
| 2 | 40.2 | 8.37 | 70182 | 61.4 | 7.21 | 381275 | 0.16 |
| 3 | 54.7 | 11.38 | 97439 | 59.6 | 6.99 | 366979 | 0.16 |
| 4 | 63.7 | 13.26 | 130086 | 61.4 | 7.21 | 401044 | 0.18 |
| | | | | Average response factor | | | 0.17 |

Yield of the Hydrogenation of CMFDBA 6 to DMF (3).

The reaction details are described above. Total mass of CMFDBA used was 2.002 g. Total volume of the reaction mixture after hydrogenation was 10.5 mL. The reaction mixture was carefully transferred into a 500 mL volumetric flask and dodecane (0.585 g, 0.00687 M) was added. The flask was filled up to the mark using dichloromethane. The area observed for DMF was 105080, and the area observed for dodecane was 354267. Using the calculation set forth above, 0.575 g were determined to be in the volumetric flask. The theoretical yield of DMF from 2.002 g of CMFDBA was 0.700 g, and the percent yield calculated by GCMS was 82%.

Using literature data for the conversion of corn stover to CMF 2 (Mascal & Nikitin, *ChemSusChem* 2009, 2, 859) an overall yield of 65% can be calculated from raw biomass to DMF 3 in just three steps. The corresponding yields of 3 from pure cellulose and sucrose would be 68 and 73%, respectively. This simple, efficient, and renewable syntheses of DMF 3 from easily accessible, biomass-derived CMF 2 via dibutyl acetal 6 will promote the wide adoption of 3 as a fuel and chemical intermediate in the rapidly emerging, green chemistry revolution—a prescient term used by Clark in the inaugural issue of *Green Chemistry* (J. H. Clark, *Green Chem.* 1999, 1, 1)

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for preparing a compound of formula I:

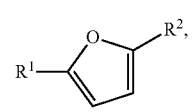

(I)

the method comprising
forming a first reaction mixture comprising a carbonyl derivatizing agent, an acid, and a compound of formula IIa

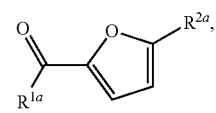

(IIa)

under conditions sufficient to form a compound of formula IIb:

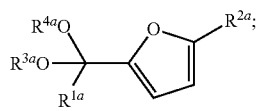

(IIb)

forming a reaction mixture comprising a catalyst, a hydrogen source, and the compound of formula IIb, under conditions sufficient to form the compound of formula I;
wherein
$R^1$ and $R^2$ are independently $C_{1-18}$ alkyl;
$R^{1a}$ is selected from the group consisting of H and $C_{1-17}$ alkyl;
$R^{2a}$ is $C_{1-18}$ haloalkyl;
$R^{3a}$ is selected from the group consisting of H, $C_{1-6}$ alkyl, and $C_{1-6}$ acyl; and
$R^{4a}$ is selected from the group consisting of $C_{1-6}$ alkyl and $C_{1-6}$ acyl, or
$R^{3a}$ and $R^{4a}$ are taken together to form $C_{2-4}$ alkylene.

2. The method of claim 1, wherein the carbonyl derivatizing agent is selected from the group consisting of an orthoester, a $C_{1-6}$ alkanol, a $C_{2-4}$ alkane-diol, an acid chloride, and an acid anhydride.

3. The method of claim 1, wherein the acid is selected from the group consisting of an acidic ion exchange resin, a sulfonic acid, sulfamic acid, and hydrochloric acid.

4. The method of claim 1, wherein $R^{2a}$ has the formula —(CHX)$R^{2b}$, wherein X is halogen and $R^{2b}$ is $C_{1-17}$ alkyl.

5. The method of claim 1, wherein $R^{2a}$ is chloromethyl.

6. The method of claim 1, wherein the compound of formula IIa is 5-(chloromethyl)furfural.

7. The method of claim 1, wherein the compound of formula I is 2,5-dimethylfuran.

8. The method of claim 1, wherein the hydrogen source is hydrogen gas.

9. The method of claim 1, wherein the catalyst is a transition metal-based catalyst.

10. The method of claim 9, wherein the catalyst is palladium on carbon.

11. The method of claim 1, comprising:

forming the first reaction mixture comprising acetic anhydride, an acidic ion exchange resin, and the compound of formula IIa having the structure:

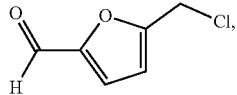

under conditions sufficient to form the compound of formula IIb having the structure:

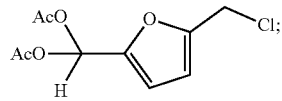

and forming the reaction mixture comprising palladium on carbon, hydrogen gas, and the compound of formula IIb, under conditions sufficient to form the compound of formula I having the structure:

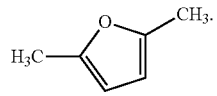

12. The method of claim 1, comprising:

forming the first reaction mixture comprising n-butanol, hydrochloric acid, and the compound of formula IIa having the structure:

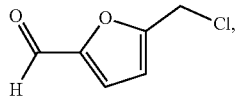

under conditions sufficient to form the compound of formula IIb having the structure:

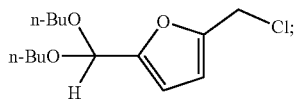

and forming the reaction mixture comprising palladium on carbon, hydrogen gas, and the compound of formula IIb under conditions sufficient to form the compound of formula I having the structure:

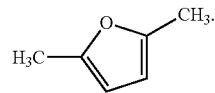

13. The method of claim 1, comprising:

forming the first reaction mixture comprising ethanol, hydrochloric acid, and the compound of formula IIa having the structure:

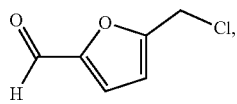

under conditions sufficient to form the compound of formula IIb having the structure:

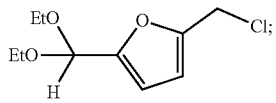

and forming the reaction mixture comprising palladium on carbon, hydrogen gas, and the compound of formula IIb under conditions sufficient to form the compound of formula I having the structure:

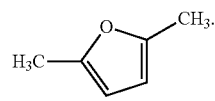

14. The method of claim 1, wherein the reaction mixture comprising the catalyst, the hydrogen source, and the compound of formula II further comprises N,N-dimethylformamide.

15. The method of any of claim 14, wherein the reaction mixture comprising the catalyst, the hydrogen source, the compound of formula II, and N,N-dimethylformamide further comprises acetic acid.

16. The method of claim 1, wherein the reaction mixture comprising the catalyst, the hydrogen source, and the compound of formula II further comprises pentane.

* * * * *